(12) United States Patent
Roth et al.

(10) Patent No.: US 8,742,125 B2
(45) Date of Patent: Jun. 3, 2014

(54) PROCESS FOR THE PREPARATION OF 2-TRIFLUOROMETHYL-5-(1-SUBSTITUTED) ALKYLPYRIDINES

(75) Inventors: Gary Alan Roth, Midland, MI (US); Douglas C. Bland, Midland, MI (US); James R. McConnell, Midland, MI (US)

(73) Assignee: Dow AgroSciences, LLC., Indianapolis, IN (US)

(*) Notice: Subject to any disclaimer, the term of this patent is extended or adjusted under 35 U.S.C. 154(b) by 0 days.

(21) Appl. No.: 13/303,182

(22) Filed: Nov. 23, 2011

(65) Prior Publication Data
US 2012/0142933 A1    Jun. 7, 2012

Related U.S. Application Data

(60) Provisional application No. 61/419,279, filed on Dec. 3, 2010.

(51) Int. Cl.
*C07D 213/00*    (2006.01)

(52) U.S. Cl.
USPC .......................................................... 546/339

(58) Field of Classification Search
None
See application file for complete search history.

(56) References Cited

U.S. PATENT DOCUMENTS

| | | | |
|---|---|---|---|
| 5,708,175 A * | 1/1998 | Koyanagi et al. | 546/250 |
| 7,541,469 B2 | 6/2009 | Renga et al. | |
| 7,678,920 B2 | 3/2010 | Zhu et al. | |
| 7,687,634 B2 | 3/2010 | Loso et al. | |
| 7,709,650 B2 | 5/2010 | Renga et al. | |
| 2008/0033180 A1* | 2/2008 | Renga et al. | 546/339 |
| 2010/0004457 A1 | 1/2010 | Bland et al. | |

FOREIGN PATENT DOCUMENTS

WO    PCT/US11/61980    3/2011

* cited by examiner

*Primary Examiner* — Heidi Reese
(74) *Attorney, Agent, or Firm* — Carl D. Corvin

(57) ABSTRACT

2-Trifluoromethyl-5-(1-substituted)alkylpyridines of formula (I)

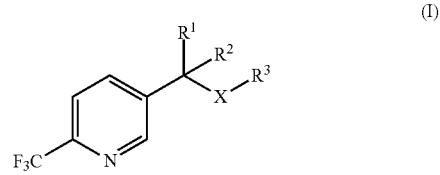

wherein
$R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represents a 3- to 6-membered saturated ring optionally substituted with an O or a N atom,
$R^3$ represents $C_1$-$C_4$ alkyl or $R^3$ taken together with either of $R^1$ or $R^2$ represent a 4- to 6-membered saturated ring, and
X represents $CH_2$, O or S,
are produced efficiently and in high yield from an 4-alkoxy-1,1,1-trifluorobut-3-en-2-one (II)

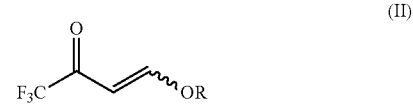

wherein
R represents a $C_1$-$C_4$ alkyl by condensation with an enamine (III)

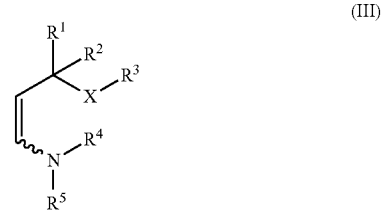

wherein
$R^1$, $R^2$, $R^3$ and X are as previously defined, and
$R^4$ and $R^5$ independently represent $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl or $R^4$ and $R^5$ taken together with N represent a 5- or 6-membered saturated or unsaturated ring,
to provide an intermediate of the formula (IV)

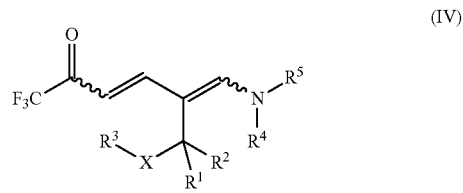

wherein
$R^1$, $R^2$, $R^3$, $R^4$, $R^5$ and X are as previously defined followed by cyclization in the presence of ammonia or a reagent capable of generating ammonia. Both reactions are performed in the same nonpolar solvent without isolation and purification of intermediates.

6 Claims, No Drawings

PROCESS FOR THE PREPARATION OF 2-TRIFLUOROMETHYL-5-(1-SUBSTITUTED) ALKYLPYRIDINES

CROSS-REFERENCE TO RELATED APPLICATIONS

This Application claims priority from U.S. provisional application 61/419,279 filed on Dec. 3, 2010. The entire content of this provisional application is hereby incorporated by reference into this Application.

BACKGROUND OF THE INVENTION

The present invention concerns an improved process for the preparation of 2-trifluoromethyl-5-(1-alkylthio)alkylpyridines from substituted enamines.

2-Trifluoromethyl-5-(1-alkylthio)alkylpyridines are useful intermediates for the preparation of certain new insecticides; see, for example, U.S. Pat. Nos. 7,678,920 and 7,687,634. U.S. Pat. Nos. 7,541,469 and 7,709,650 describe, inter alia, the condensation of a 4-alkoxy-1,1,1-trifluorobut-3-en-2-one with an enamine and the subsequent cyclization in the presence of ammonia or a reagent capable of generating ammonia. U.S. Patent Publication 2010-0004457 describes, inter alia, the condensation of a 4-chloro-4-alkoxy-1,1,1-trifluoro-2-butanone with an enamine in the presence of a tertiary amine base to provide a dienamine intermediate and its subsequent cyclization in the presence of ammonia or a reagent capable of generating ammonia. It would be desirable to have a process starting with 4-alkoxy-1,1,1-trifluorobut-3-en-2-one in which the condensation and cyclization reactions could be performed in the same convenient solvent and the unit operations could be reduced without decreasing overall reaction yield.

SUMMARY OF THE INVENTION

The present invention concerns an improved process for the preparation of 2-trifluoromethyl-5-(1-substituted)alkylpyridines. More particularly, the present invention concerns an improved process for the preparation of a 2-trifluoromethyl-5-(1-substituted)alkylpyridine (I),

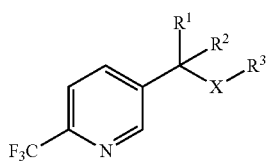

wherein $R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represents a 3- to 6-membered saturated ring optionally substituted with an O or a N atom, $R^3$ represents $C_1$-$C_4$ alkyl or $R^3$ taken together with either of $R^1$ or $R^2$ represent a 4- to 6-membered saturated ring, and X represents $CH_2$, O or S, in which i) an 4-alkoxy-1,1,1-trifluorobut-3-en-2-one of the formula (II)

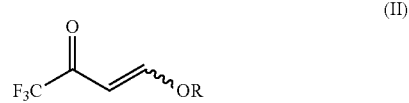

in which R represents a $C_1$-$C_4$ alkyl is condensed with an enamine (III)

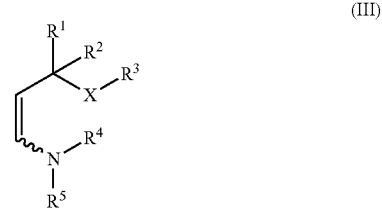

wherein $R^1$, $R^2$, $R^3$ and X are as previously defined, and $R^4$ and $R^5$ independently represent $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl or $R^4$ and $R^5$ taken together with N represent a 5- or 6-membered saturated or unsaturated ring, to provide an intermediate of the formula (IV)

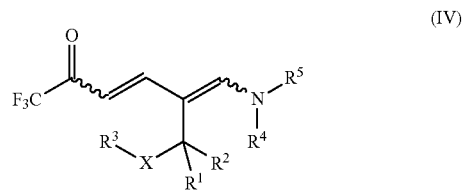

wherein $R^1$, $R^2$, $R^3$, $R^4$, $R^5$ and X are as previously defined, and ii) the intermediate of the formula (IV) is cyclized in the presence of ammonia or a reagent capable of generating ammonia, the improvement comprising conducting both steps in a nonpolar solvent without isolation or purification of the condensation intermediate IV.

In the preferred embodiments of the present invention, $R^1$ and $R^2$ independently represent H or methyl, $R^3$ represents methyl and X represents S.

DETAILED DESCRIPTION OF THE INVENTION

Unless specifically limited otherwise, the term "alkyl" (including derivative terms such as "haloalkyl", "alkoxyalkyl", "alkylaminoalkyl" and "arylalkyl"), as used herein, include straight chain, branched chain, and cyclic groups. Thus, typical alkyl groups are methyl, ethyl, 1-methylethyl, propyl, 1,1-dimethylethyl, and cyclopropyl. The term "alkenyl", as used herein, includes straight chain, branched chain, and cyclic groups and is intended to include one or more unsaturated bonds. The term "halogen" includes fluorine, chlorine, bromine and iodine. The term "haloalkyl" includes alkyl groups substituted with from one to the maximum possible number of halogen atoms. The term "aryl", as well as derivative terms such as "arylalkyl", refers to a phenyl or naphthyl group. The term "heteroaryl" refers to a 5- or 6-membered aromatic ring containing one or more heteroatoms, viz., N, O or S; these heteroaromatic rings may be fused to other aromatic systems.

In the present invention, a 2-trifluoromethyl-5-(1-substituted)alkylpyridine (I),

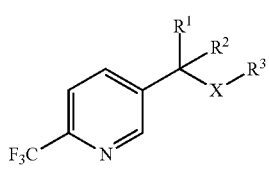

(I)

wherein $R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represents a 3- to 6-membered saturated ring optionally substituted with an O or a N atom;

$R^3$ represents $C_1$-$C_4$ alkyl or $R^3$ taken together with either of $R^1$ or $R^2$ represent a 4- to 6-membered saturated ring; and X represents $CH_2$, O or S;

is prepared by condensing a 4-alkoxy-1,1,1-trifluorobut-3-en-2-one of the formula (II):

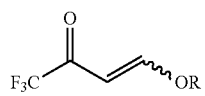

(II)

in which R represents a $C_1$-$C_4$ alkyl
with an enamine (III)

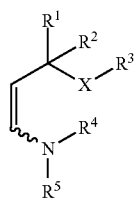

(III)

wherein $R^1$, $R^2$, $R^3$ and X are as previously defined; and $R^4$ and $R^5$ independently represent $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl or $R^4$ and $R^5$ taken together with N represent a 5- or 6-membered saturated or unsaturated ring to provide an intermediate of the formula (IV)

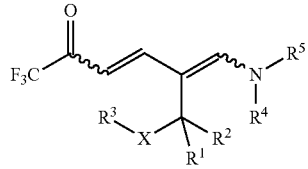

(IV)

wherein $R^1$, $R^2$, $R^3$, $R^4$, $R^5$ and X are as previously defined; and by cyclizing the intermediate of the formula (IV) in the presence of ammonia or a reagent capable of generating ammonia. The improvement in the process comprises conducting both steps in a nonpolar solvent without isolation or purification of the condensation intermediate IV.

In the first step of the present invention, the 4-alkoxy-1,1,1-trifluorobut-3-en-2-one of the formula (II):

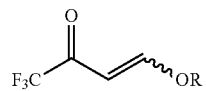

(II)

in which R represents a $C_1$-$C_4$ alkyl
is reacted with an enamine (III)

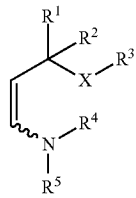

(III)

wherein $R^1$, $R^2$, $R^3$, $R^4$, $R^5$ and X are as previously defined to provide an intermediate of the formula (IV)

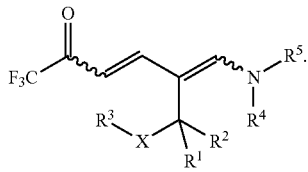

(IV)

Enamines (III) can be conveniently prepared from the addition of a suitably substituted amine to an appropriately substituted aldehyde in the presence of a water adsorbing material, with or without a suitable solvent. Typically, the appropriately substituted aldehyde, for example 3-alkylthiopropionaldehyde, is reacted with an anhydrous disubstituted amine, for example pyrrolidine, at about −20° C. to about 20° C. in the presence of a desiccant such as anhydrous potassium carbonate, and the product is isolated by routine procedures and usually used without further purification.

Approximately equimolar quantities of the 4-alkoxy-1,1,1-trifluorobut-3-en-2-one (II) and the enamine (III) are required in the condensation process.

The condensation is conducted at a temperature from about −20° C. to about 35° C. Temperatures from about −5° C. to about 20° C. are usually preferred.

This condensation is preferably conducted in a non-polar solvent. Preferred non-polar solvents include hydrocarbon and aromatic hydrocarbon solvents, most preferably toluene.

It is preferred that the 4-alkoxy-1,1,1-trifluorobut-3-en-2-one (II) should be added to a preformed mixture of the enamine (III).

In a typical condensation reaction, the enamine (III) is dissolved in the desired non-polar solvent at about −5° C. to about 20° C. and 4-alkoxy-1,1,1-trifluorobut-3-en-2-one (II) is continuously added via addition funnel to this solution. The mixture is agitated until the 4-alkoxy-1,1,1-trifluorobut-3-en-2-one (II) and enamine (III) are consumed. With the use of a nonpolar solvent like toluene, intermediate (IV) can be used as is without further isolation or purification.

In the final step of the process, the intermediate of the formula (IV)

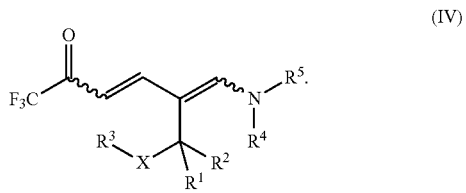

(IV)

is cyclized in the presence of ammonia or a reagent capable of generating ammonia to provide the desired 2-trifluoromethyl-5-(1-substituted) alkylpyridine (I).

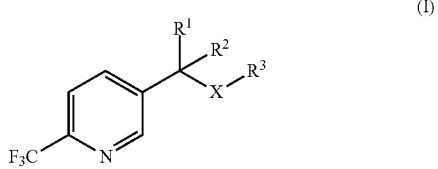

(I)

Typical reagents capable of generating ammonia include, for example, 1) an ammonium salt of an acid, preferably an organic acid, 2) formamide, or 3) formamide with an acid or acid salt. The ammonium salt of any aliphatic or aromatic organic acid can be used, but for convenience of processing, the ammonium salts of $C_1$-$C_4$ alkanoic acids are preferred. Ammonium formate and ammonium acetate are most preferred.

Approximately equimolar quantities of the intermediate (IV) and ammonia or reagents capable of generating ammonia are required in the cyclization process, although 2-4 fold excesses of the ammonia or the ammonia precursor are often preferred.

This cyclization is conducted in the same non-polar solvent as the condensation.

The reaction is conducted at a temperature from about ambient temperature to about 150° C. Temperatures from about 45° C. to about 110° C. are usually preferred.

The product is isolated by conventional techniques such as silica gel chromatography or fractional distillation.

In a typical cyclization reaction, the ammonium salt of an organic acid is added to the intermediate (IV) directly from the condensation reaction, and the mixture is heated until the reaction is complete. The reaction mixture can be washed with water and optionally brine, and the 2-trifluoromethyl-5-(1-substituted)alkylpyridine (I) can be isolated by vacuum distillation.

The following examples are presented to illustrate the invention.

EXAMPLES

Example 1

Preparation of 1,1,1-Trifluoro-6-methylthio-5-(pyrrolidin-1-ylmethylene)hept-3-en-2-one

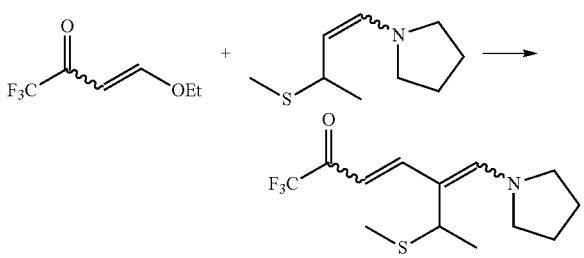

A) A solution of 1-(pyrrolidin-1-yl)-3-methylthio-1-butene in toluene (396.98 g, 29.43 wt %, 116.83 g, 0.682 moles) was poured into a 1-liter (L) 3-necked round bottom flask equipped with a magnetic stirrer, internal thermometer, pressure equalizing addition funnel with nitrogen oil bubbler and a stopper. The stirred solution was chilled in an ice bath to <5° C. 4-Ethoxy-1,1,1-trifluoro-but-3-ene-2-one (128.2 g, 0.763 moles, 1.12 equivalents (equiv)) was added to the cold, stirred enamine solution via the addition funnel over 52 minutes (min). The initial temperature was 2.2° C., the final temperature was 3.5° C. and a maximum temperature of 5.0° C. was reached during the addition. The reaction mixture was allowed to slowly warm to room temperature and stirred overnight. The dark red reaction mixture was sampled and analyzed by cool on-column (COC) gas chromatography (GC). COC GC analysis gave, on a normalized area % basis: unreacted enamine (8.2 area %), 1,1,1-trifluoro-4-(pyrrolidin-1-yl)but-3-en-2-one impurity (11.3 area %) and 1,1,1-trifluoro-6-methylthio-5-(pyrrolidin-1-ylmethylene)hept-3-en-2-one product (80.5 area %). The crude product solution (522.70 g) was then transferred to a glass sample bottle for use in subsequent experiments. For the purpose of determining ammonia loadings in the subsequent experiments, the conversion was assumed to be 100% or 1.305 mmoles dienamine/gram of solution.

B) Toluene (330 g) was added to a 63 wt % 1-(pyrrolidin-1-yl)-3-methylthio-1-butene/toluene solution (173.18 g, 0.634 moles of enamine) in a 1-L 3-necked round bottom flask equipped with a magnetic stirrer, pressure equalizing addition funnel with nitrogen oil bubbler and stopper. The stirred solution was chilled to <5° C. in an ice bath. 1,1,1-trifluoro-but-3-ene-2-one (117.11 g, 0.697 moles, 1.10 equiv) was added dropwise via the addition funnel to the stirred, chilled solution over 33 min. A maximum temperature of 7.0° C. was reached. The ice bath was removed and the reaction mixture was allowed to warm to room temperature with stirring overnight. The entire dark red reaction mixture (668.92 g) was transferred to a glass sample bottle. The solution was assumed to contain 0.9463 mmoles 1,1,1-trifluoro-6-methylthio-5-(pyrrolidin-1-ylmethylene)hept-3-en-2-one product/gram of solution (i.e.

100% conversion from enamine) for the purposes of determining subsequent loading amounts. The solution was used directly in the following experiments.

C) A 1-(pyrrolidin-1-yl)-3-methylthio-1-butene/toluene solution (178.96 g, 39.1 wt % enamine, 69.97 g, 0.408 moles) was added to a 500-milliliter (mL) 3-necked jacketed glass reactor equipped with an overhead mechanical stirrer with Teflon paddle, glass thermowell with K-thermocouple, Teflon load line connected to a ProMinent pump for 1,1,1-trifluoro-but-3-ene-2-one loading and a reflux condenser with nitrogen oil bubbler. Toluene (122.38 g) was added to adjust the enamine concentration to 23.2 wt %. The stirred solution was chilled to <5° C. 1,1,1-Trifluoro-but-3-ene-2-one (77.18 g, 97 area % purity, 74.86 g, 0.445 moles, 1.09 equiv) was poured into a nitrogen-padded delivery bottle with a line to the ProMinent pump. The 1,1,1-trifluoro-but-3-ene-2-one was added via the ProMinent addition pump over 36 min. The temperature during the addition did not exceed 5° C. Stirring was continued at <5° C. for 30 min. The reaction mixture was warmed to about 25° C. and stirred for an additional 5 hours (h). Agitation was stopped and the reaction allowed to stand at 25° C. under nitrogen for 2 days (d). The 1,1,1-trifluoro-6-methylthio-5-(pyrrolidin-1-ylmethylene)hept-3-en-2-one product/toluene solution was drained from the reactor and the reactor was rinsed with toluene (3×50 mL) and added to the drained reactor contents. The 1,1,1-trifluoro-6-methylthio-5-(pyrrolidin-1-ylmethylene)hept-3-en-2-one product/toluene solution (251.06 g) was analyzed by $^1$H-NMR spectroscopy using pyrazine as an internal standard with a pulse delay of 90 seconds (sec) and indicated a 79% yield of 1,1,1-trifluoro-6-methylthio-5-(pyrrolidin-1-ylmethylene)hept-3-en-2-one product from enamine.

Example 2

Preparation of 5-(1-(Methylthio)ethyl)-2-(trifluoromethyl)pyridine

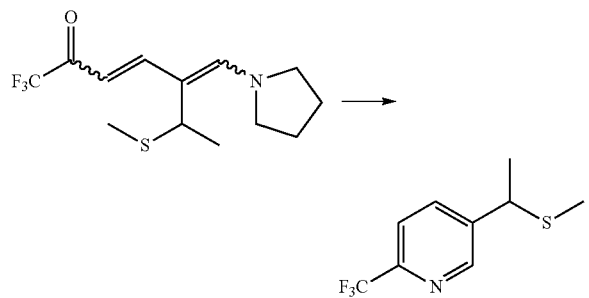

A) To a 500-mL round bottom flask equipped with a magnetic stirrer, a Claisen head adapter with reflux condenser and nitrogen oil bubbler vented to a water scrubber, and a septum through which was inserted a K-thermocouple and a Teflon load line for ammonia delivery were added 1,1,1-trifluoro-6-methylthio-5-(pyrrolidin-1-ylmethylene)hept-3-en-2-one solution in toluene (285.82 g, 0.373 moles of dienamine) and glacial acetic acid (33.73 g, 0.562 moles, 1.51 equiv). The solution was cooled with stiffing to <5° C. in an ice bath. Anhydrous ammonia (9.53 g, 0.560 moles, 1.50 equiv) was charged to the reactor contents through the Teflon load line (sub-surface). The reaction temperature increased from 0.8° C. to 6.9° C. during the first 12 min of the addition and a thick slurry developed. The addition was paused and toluene (50 mL) was added. The addition was resumed but paused again after 18 min because a thick slurry was again present. The internal temperature was 11.3° C. Additional toluene (20 mL) was added. The ammonia addition was resumed and was completed in 6 min. The total addition time was 36 min and the final temperature was 5.0° C. The ice bath was removed and a heating mantle was installed. The dark slurry was heated to about 85° C. and was stirred for 1 h. During the heat-up the solids dissolved. The heating mantle was turned off and the reaction mixture was allowed to cool to room temperature. Stirring was continued over the weekend. The water scrubber had a pH of approximately 7. The crude reaction mixture (385.06 g) was transferred to a glass sample bottle. A portion was analyzed by GC using dibutyl phthalate as an internal standard, and the analysis showed 18.6 wt % 5-(1-(methylthio)-ethyl)-2-(trifluoromethyl)pyridine for a yield of 87%. On a normalized area % basis the GC analysis showed 17% 1,1,1-trifluoro-4-(pyrrolidin-1-yl)but-3-en-2-one impurity carried over from the starting 1,1,1-trifluoro-6-methylthio-5-(pyrrolidin-1-ylmethylene)hept-3-en-2-one solution in toluene and 83% for 5-(1-(methylthio)ethyl)-2-(trifluoromethyl)pyridine.

B) A 500 mL round bottom flask was fitted with a Claisen head adapter to which was affixed a water-cooled reflux condenser with nitrogen oil bubbler vented to a water scrubber. The remaining neck was fitted with a septum through which a K-thermocouple and Teflon load line for ammonia delivery were inserted. Stirring was accomplished with a magnetic stirrer and bar. To the 500 mL reactor were added 1,1,1-trifluoro-6-methylthio-5-(pyrrolidin-1-ylmethylene)hept-3-en-2-one/toluene solution (219.8 g, 0.208 moles of dienamine) and glacial acetic acid (18.74 g, 0.312 moles, 1.5 equiv). The stirred solution was cooled to <5° C. in an ice bath. Anhydrous ammonia (5.30 g, 0.312 moles, 1.5 equiv) was sparged into the reaction mixture over 14 min during which time a maximum temperature of 14.7° C. was achieved. A thick, but stirrable, slurry formed. The ice bath was removed and the reaction mixture was heated at reflux (>85° C.) with a heating mantle. Stirring was continued for 1 h at a temperature of 86 to 89° C. Heating was stopped, the reaction mixture was allowed to cool to room temperature and was stirred overnight. The reaction mixture (238.71 g) was transferred to a glass sample bottle. A sample was analyzed by GC using dibutyl phthalate as an internal standard, and the analysis showed 17 wt % of 5-(1-(methylthio)ethyl)-2-(trifluoromethyl)pyridine for an in-pot yield of 88%.

C) A crude 1,1,1-trifluoro-6-methylthio-5-(pyrrolidin-1-ylmethylene)hept-3-en-2-one/toluene solution (114.59 g, 0.150 moles of dienamine) and additional toluene (50 mL) were combined in a 500 mL round bottom flask equipped as described for Procedure 2A above. The stirred solution was cooled in an ice bath to <5° C. Anhydrous ammonia (5.09 g, 0.299 moles, 2.0 equiv) was added through the Teflon load line (sub-surface) to the stirred reaction mixture over 8 min. The starting temperature was 0.5° C. and the temperature at the end of the addition was 0.3° C. The ice bath was removed and the reaction mixture was allowed to warm to room temperature over 30 min. The reaction mixture was heated at about 84° C. and stirred for 1 h. During the heating significant degassing occurred at about 30° C. The reaction mixture was allowed to cool to room temperature and was stirred over the weekend. The pH of the water scrubber was approximately 10, indicating loss of ammonia from the reaction mixture. The crude reaction mixture (156.56 g) was transferred to a glass sample bottle. A portion was analyzed by GC using dibutyl phthalate as an internal standard, and the result was 13.5 wt % 5-(1-(methylthio)ethyl)-2-(trifluoromethyl)pyridine for a yield of 64%. On a normalized area % basis the GC analysis showed 24% 1,1,1-trifluoro-4-(pyrrolidin-1-yl)but-3-en-2-one impurity and 76% 5-(1-(methylthio)ethyl)-2-(trifluoromethyl)pyridine.

D) A 500 mL round bottom flask was fitted with a Claisen head adapter to which was affixed a dry ice/acetone reflux condenser with nitrogen oil bubbler vented to a water scrubber. The remaining neck was fitted with a septum through which a K-thermocouple and Teflon load line for ammonia delivery were inserted. Stirring was accomplished with a magnetic stirrer and bar. To the 500 mL reactor was added a solution of the 1,1,1-trifluoro-6-methylthio-5-(pyrrolidin-1-ylmethylene)hept-3-en-2-one (149.0 g, 0.141 moles of dienamine) in toluene and the stirred solution was cooled to <5° C. in an ice bath. Anhydrous ammonia (4.79 g, 0.282 moles, 2.0 equiv) was sparged into the reaction mixture over 13 min. A maximum temperature of 5.2° C. was observed. The reaction mixture developed a greenish color during the addition. The ice bath was removed and the reaction mixture was heated at reflux (45 to 50° C.). A higher reflux temperature could not be achieved due to the return of the cold liquid ammonia from the dry ice/acetone condenser. Stirring was continued for one hour and then the heat was shut off and the reaction mixture allowed to cool to room temperature and was stirred overnight. The reaction mixture (151.21 g) was transferred to a glass sample bottle. A sample was analyzed by GC using dibutyl phthalate as an internal standard, and the analysis showed 14.8 wt % 5-(1-(methylthio)ethyl)-2-(trifluoromethyl)pyridine for an in-pot yield of 72%.

E) A 1,1,1-trifluoro-6-methylthio-5-(pyrrolidin-1-ylmethylene)hept-3-en-2-one/toluene solution (50.05 g, 0.0474 moles of dienamine) was loaded into a 100 mL stainless steel Parr reactor. The system was sealed, pressure tested and purged with nitrogen and the agitation set to 250 revolutions per minute (rpm). Anhydrous ammonia (1.61 g, 0.0947 moles, 2.0 equiv) was charged to the Parr reactor. The initial temperature was 23° C. and increased to 27° C. The pressure increased from 0 pounds per square inch gauge (psig; about 101 kilopascals (kPa)) to 73 psig (about 605 kPa) and then decreased to 40 psig (about 376 kPa) after the addition was complete. The ammonia cylinder was pressurized with nitrogen (200 psig (about 1480 kPa)) and the cylinder contents vented into the Parr reactor. The final reactor pressure was 84 psig (about 681 kPa). The reactor was set to an initial temperature set point (SP) of 65° C. The table below summarizes the rest of the run time data.

| Time | Pressure (psig) | Temperature (° C.) | Comments |
|---|---|---|---|
| 10:15 | 84 (~681 kPa) | 26 | |
| 10:20 | 94 (~749 kPa) | 54 | |
| 10:23 | 106 (~832 kPa) | 65 | Temp SP to 75° C. |
| 10:25 | 118 (~915 kPa) | 75 | Temp SP to 80° C. |
| 10:27 | 129 (~991 kPa) | 83 | |
| 10:30 | 137 (~1046 kPa) | 86 | |
| 10:45 | 131 (~1005 kPa) | 78 | Temp SP to 85° C. |
| 11:00 | 153 (~1156 kPa) | 89 | |
| 11:20 | 150 (~1136 kPa) | 86 | |
| 11:35 | 148 (~1122 kPa) | 85 | Heater shut-off |

The reactor contents were allowed to cool for about 2 h at which time the internal temperature was 26° C. The reactor was vented to an aqueous acetic acid scrubber. This was followed by pressurizing the reactor to 80 psig (about 653 kPa) with nitrogen and venting to the aqueous acetic acid scrubber five times. The reactor was opened, and the crude reaction mixture (49.40 g) transferred to a glass sample bottle. A portion was analyzed by GC using dibutyl phthalate as an internal standard. Analysis gave 21 wt % of 5-(1-(methylthio)ethyl)-2-(trifluoromethyl)-pyridine for a yield of 80%.

What is claimed is:
1. A process for the preparation of a 2-trifluoromethyl-5-(1-substituted)-alkylpyridine (I),

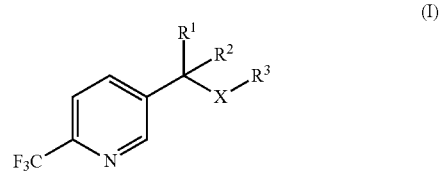

wherein
$R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represents a 3- to 6-membered saturated ring optionally substituted with an O or a N atom,
$R^3$ represents $C_1$-$C_4$ alkyl or $R^3$ taken together with either of $R^1$ or $R^2$ represent a 4- to 6-membered saturated ring, and
X represents $CH_2$, O or S,
in which:
i) an 4-alkoxy-1,1,1-trifluorobut-3-en-2-one of the formula (II)

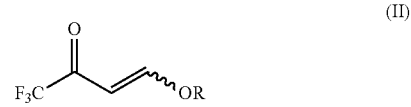

in which R represents a $C_1$-$C_4$ alkyl
is condensed with an enamine (III)

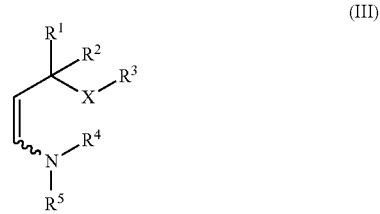

wherein

R$^1$, R$^2$, R$^3$ and X are as previously defined, and

R$^4$ and R$^5$ independently represent C$_1$-C$_8$ alkyl, C$_2$-C$_8$ alkenyl, C$_1$-C$_8$ arylalkyl, C$_1$-C$_8$ haloalkyl, C$_1$-C$_8$ alkoxyalkyl, C$_1$-C$_8$ alkylaminoalkyl, aryl or heteroaryl or R$^4$ and R$^5$ taken together with N represent a 5- or 6-membered saturated or unsaturated ring, to provide an intermediate of the formula (IV)

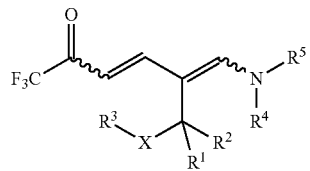

(IV)

wherein

R$^1$, R$^2$, R$^3$, R$^4$, R$^5$ and X are as previously defined, and ii) the intermediate of the formula (IV) is cyclized in the presence of ammonia or a reagent capable of generating ammonia, the improvement comprising conducting both steps in a non-polar solvent without isolation or purification of the condensation intermediate IV.

2. A process according to claim 1 wherein R$^1$ and R$^2$ independently represent H or methyl, R$^3$ represents methyl and X represents S.

3. A process according to claim 1 wherein the molecule of formula (II) is condensed with an enamine (III) at a temperature from about −20° C. to about 35° C.

4. A process according to claim 1 wherein the molecule of formula (II) is condensed with an enamine (III) at a temperature from about −5° C. to about 20° C.

5. A process according to claim 1 wherein said non-polar solvent is toluene.

6. A process according to claim 2, 3, or 4, wherein said non-polar solvent is toluene.

* * * * *